United States Patent [19]

Martin et al.

[11] Patent Number: 5,788,155

[45] Date of Patent: Aug. 4, 1998

[54] AIR FRESHENER DISPENSER DEVICE WITH DUAL CARTRIDGE CAPACITY

[75] Inventors: John Martin; Joseph M. Rosplock, both of Caledonia, Wis.

[73] Assignee: S. C. Johnson & Son, Inc., Racine, Wis.

[21] Appl. No.: 672,799

[22] Filed: Jun. 28, 1996

[51] Int. Cl.⁶ .................................................. F17C 13/00
[52] U.S. Cl. .................................................. 239/34
[58] Field of Search ............................. 206/461, 463; 239/34, 56–60, 600

[56] References Cited

U.S. PATENT DOCUMENTS

| | | |
|---|---|---|
| Re. 32,513 | 10/1987 | Seaber et al. . |
| 1,679,561 | 8/1928 | Cantrell ...................... 239/71 X |
| 2,481,296 | 10/1949 | Dupuy . |
| 2,594,714 | 12/1952 | Andre . |
| 3,055,297 | 9/1962 | Leeds ...................... 101/327 |
| 3,192,681 | 7/1965 | Greenbaum ...................... 206/463 X |
| 3,790,081 | 2/1974 | Thornton et al. . |
| 3,946,945 | 3/1976 | Odioso et al. . |
| 4,130,245 | 12/1978 | Bryson . |
| 4,145,001 | 3/1979 | Weyenberg et al. . |
| 4,157,787 | 6/1979 | Schwartz . |
| 4,158,440 | 6/1979 | Sullivan et al. . |
| 4,220,281 | 9/1980 | Martens, III et al. . |
| 4,306,679 | 12/1981 | Dusek et al. . |
| 4,382,548 | 5/1983 | van der Heijden . |
| 4,502,630 | 3/1985 | Haworth et al. . |
| 4,558,820 | 12/1985 | Harris, Jr. . |
| 4,583,686 | 4/1986 | Martens et al. . |
| 4,595,925 | 6/1986 | Hansen . |
| 4,605,165 | 8/1986 | Van Loveren et al. . |
| 4,615,486 | 10/1986 | Konicek . |
| 4,630,775 | 12/1986 | Mandon et al. . |
| 4,660,763 | 4/1987 | Gutkowski et al. . |
| 4,739,928 | 4/1988 | O'Neil . |
| 4,849,606 | 7/1989 | Martens, III et al. . |
| 4,948,047 | 8/1990 | Zembrodt . |
| 4,960,240 | 10/1990 | McElfresh . |
| 4,983,578 | 1/1991 | Cashman et al. . |
| 4,998,671 | 3/1991 | Leifheit . |
| 5,054,610 | 10/1991 | Ajello ...................... 206/461 X |
| 5,230,867 | 7/1993 | Kunze et al. ...................... 239/56 X |
| 5,344,018 | 9/1994 | Severin ...................... 206/469 |
| 5,439,100 | 8/1995 | Gordon et al. . |

*Primary Examiner*—Kevin Weldon

[57] ABSTRACT

This invention provides an air freshener dispenser device which consists of twin cartridges which are connected end-to-end with a flexible hinge means. The two cartridges can be folded together and incorporated in a dispensing holder as multiple refill units. Each cartridge is composed of a shallow tray which contains a volatile air freshener medium, and which has its open surface sealed with a coextensive bonded laminate of an inner vapor-permeable membrane and an outer peelable vapor-impermeable membrane. Removal of the peelable vapor-impermeable membrane sealing the two trays allows delivery of the air freshener medium as vapor into the environment at a controlled rate over an extended period of time.

13 Claims, 1 Drawing Sheet

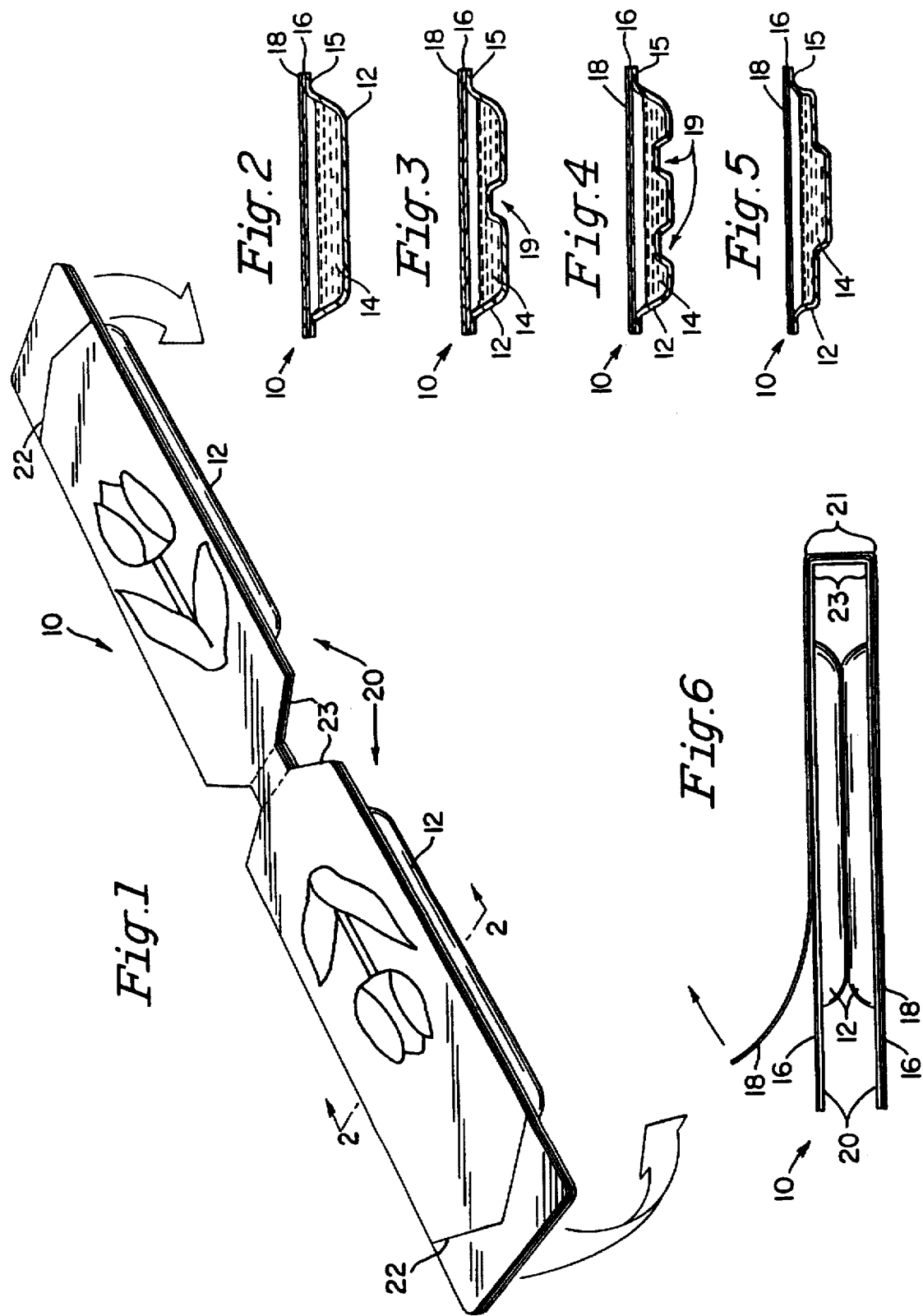

5,788,155

1

AIR FRESHENER DISPENSER DEVICE WITH DUAL CARTRIDGE CAPACITY

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks and liquid wicks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product. Such products are considered advantageous when compared with the many air-treating products for which the rate of vapor release drops substantially over the life of the product.

Products of the type having a sheet of permeable polymeric material to control the emission of air-treating vapors may be in a variety of forms. In some, the polymeric sheet covers a cylindrical container, while in others the liquid air-treating material is trapped between the permeable sheet and an impermeable plastic sheet. In still others, the permeable polymeric material forms a flexible pouch having a content of the air-treating liquid. The liquid, prior to activation, is isolated within a breakable container such as a glass vial or an impermeable plastic inner pouch, or the like.

Publications of background interest in connection with air freshener devices include U.S. Pat. Nos. 2,481,296; 2,594,714; 3,790,081; 3,946,945; 4,130,245; 4,145,001; 4,220,281; 4,306,679; 4,382,548; 4,502,630; 4,558,820; 4,583,686; 4,595,925; 4,615,486; 4,660,763; 4,630,775; 4,739,928; 4,849,606; 4,948,047; 4,960,240; 4,983,578; 4,998,671; and the like; incorporated by reference.

U.S. Pat. No. 4,157,787 describes an air freshener device which consists of a container with an open topside. The open topside is bordered by a peripheral flange, and the container has a content of a volatile ingredient. The topside of the container is sealed with two coextensive layers of thin plastic film bonded to the peripheral flange surface. The inner layer is a vapor-permeable film, and the outer layer is a peelable vapor-impermeable film.

Some air freshener dispensers are expensive to manufacture. Other air freshener dispensers are inexpensive to produce, but tend to have inferior construction and functionality.

There remains a need for a well-constructed air freshener dispenser device which can be mass-produced economically

2 and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a semi-rigid plastic assembly that can be produced economically by a thermoforming means.

It is another object of this invention to provide an air freshener dispenser device that consists of multiple cartridges which provide a more versatile range of air freshener dispensing functionality.

It is another object of this invention to provide an air freshener dispenser device which has a pair of cartridge units which are connected end-to-end by a flexible hinge means.

It is a further object of this invention to provide an air freshener dispenser device with dual rigidly supported reservoir enclosures which respectively have a volatile air freshener content, and which respectively have a topside sealed with a translucent or transparent permeable membrane.

Other objects and advantages of the present invention shall become apparent from the accompanying description and drawings.

SUMMARY OF THE INVENTION

One or more objects of the present invention are accomplished by the provision of an air freshener dispenser device consisting of an attached pair of identical cartridge units which are connected end-to-end by a flexible hinge means, wherein each cartridge is a structural assembly comprising:

(a) an elongated shallow tray having side walls with an upper edge flange which forms a peripheral margin around the open space of the tray;

(b) a thin membrane which covers the open space of the tray and is bonded to the flange peripheral margin, and the membrane forms a sealed reservoir enclosure within the tray interior, and the said membrane is permeable to a volatile medium in the reservoir enclosure;

(c) a volatile air freshener medium which is contained within the reservoir enclosure; and (d) a thin peelable impermeable membrane which is laminated coextensively with the permeable membrane to prevent volatilization of the air freshener medium through the permeable membrane from the reservoir enclosure.

DESCRIPTION OF THE DRAWINGS

FIG. 1 is a perspective view of an invention air freshener dispenser device with an imprinted design.

FIG. 2 is a cross-sectional view taken along lines 2—2 of FIG. 1.

FIGS. 3–5, respectively, illustrate alternative reservoir configurations for the tray interior and volume of air freshener ingredient taken along lines 2—2 of FIG. 1.

FIG. 6 is a side view of a FIG. 1 air freshener dispenser device which is folded in a tray-bottom to tray-bottom configuration of the twin cartridges.

DESCRIPTION OF THE PREFERRED EMBODIMENTS

FIG. 1 illustrates a present invention air freshener dispenser device 10 which has a design imprinted on the upper surface of each cartridge.

A FIG. 1 type of air freshener dispenser device has a semi-rigid structure, and its typical dimensions are about nine inches in length, about one half to one inch in width, and about one sixteenth to one half inch in thickness.

A FIG. 1 type of air freshener dispenser device can be utilized by peeling the outer impermeable membrane partially or completely from one cartridge, or peeling the outer impermeable membrane from each of the twin cartridges.

FIG. 2 is a cross-sectional end view of a FIG. 1 type of air freshener dispenser cartridge which has tray 12 and air freshener ingredient 14, and a flange 15 which is seal-bonded with inner thin film vapor-permeable membrane 16 and coextensive outer thin film vapor-impermeable membrane 18.

FIG. 3 is a cross-sectional end view similar to FIG. 2, in which centrally disposed structural reinforcing rib 19 extends along the bottom surface of tray 12. FIG. 4 is a cross-sectional end view similar to FIG. 3, in which two spaced structural reinforcing ribs 19 extend along the bottom surface of tray 12. Rib 19 can have a configuration which is adapted to key tray 12 into a conformational slotted space in a dispensing housing structure. FIG. 5 is a cross-sectional end view of an alternative reservoir configuration with a stepped structure.

FIG. 6 is a side view of a FIG. 1 air freshener device, which has cartridges 20 folded 90° C. with trays 12 in a bottom-to-bottom configuration. Cartridges 20 are folded along seams 21. FIG. 6 also illustrates the partial removal of membrane 18 from the surface of membrane 16 of the upper positioned cartridge 20.

Tray 12 of each cartridge 20 can be constructed by either injection or thermoform molding of a thermoplastic polymer such as polyethylene, polypropylene, polyvinyl chloride, and the like. In a preferred embodiment, end-to-end attached trays 12, and interconnecting flexible hinge band 23, are thermoformed as a unitary structure, and optionally include folding seams 21 to facilitate a 90° C. folding of cartridges 20.

Thin film vapor-impermeable membrane 18 is bonded to thin film vapor-permeable membrane 16 in the form of a laminate. Vapor-impermeable membrane 18 is peelable, so that its removal allows air freshener ingredient 14 to migrate through vapor-permeable membrane 16 and volatilize into the atmosphere. Peelable membrane 18 can be adapted for removal from both cartridge units at the same time, or from each cartridge unit at different times.

Vapor-permeable membrane 16 can be in the form of a flexible thin film of a thermoplastic polymer such as polyethylene, isotactic polypropylene, cellulose acetate, and the like. Membrane 16 permits migration of the enclosed volatile air freshener ingredient 14, either as a liquid or a vapor, depending on the type of membrane 16 being employed. Membrane 16 can be a microporous type (submicron pores), such as isotactic hydrophobic polypropylene film sold under the CELGARD tradename (Celanese). Microporous thermoplastic polymer films are described in U.S. Pat. No. 3,055,297; incorporated by reference.

Vapor-impermeable membrane 18 can be in the form of a flexible thin film such as aluminum foil or nylon film, which is peelable from its adhering bond to vapor-permeable membrane 16.

In a preferred embodiment a laminate of membrane 16 and membrane 18 is preformed, and then applied to tray 12 to cover the open interior, and heat-sealed along periphery flange 15 to enclose the reservoir content of air freshener ingredient 14. Production of a laminate of permeable and impermeable membranes is illustrated in U.S. Pat. No. 4,145,001; incorporated by reference.

In another preferred embodiment the membrane laminate is not heat-sealed to periphery flange 15 at the respective ends of twin cartridges 20. In FIG. 1 the heat-sealing of the membrane laminate end sections is shown as chevron-shaped heat-seal 22. This facilitates manual gripping and peeling of membrane 18 from membrane 16.

Air freshener ingredient 14 can be any air treating material which can migrate through membrane 16 and disperse into the atmosphere in vapor form. Typically air freshener ingredient 14 is a fragrance or a deodorant in liquid or gel form.

Preferably, air freshener ingredient 14 is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance also can be formed into a thixotropic gel by the addition of a thickening agent, such as fumed silica of the type marketed under the Cabosil trademark (Cabot Corporation).

A fragrance ingredient also can be in the form of a crystalline solid, which have the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treating capability to an air freshener dispenser device.

A present invention air freshener dispenser device can be produced in a continuous process by providing a moving band of thermoformed end-to-end hinged trays in repeating unitary sections, in combination with an air freshener filling station, and a moving band of flexible membrane laminate in contacting and sealing proximity with the flanges of the filled trays. The unitary sections are cut and trimmed from the moving band at the terminal end of the production line.

A present invention air freshener device can be produced in high volume from relatively inexpensive plastic materials. After usage, the device qualifies for disposal as a non-hazardous solid waste.

The present invention also contemplates an integrated combination of a FIG. 1 type air freshener device and a dispensing holder structure. The FIG. 1 device then functions as a replaceable assembly having a dual refill cartridge capacity.

What is claimed is:

1. An air freshener dispenser device consisting of an attached pair of identical cartridge units which are connected end-to-end by a flexible hinge means, wherein each cartridge is a structural assembly comprising:

(a) An elongated shallow tray having side walls with an upper edge flange which forms a peripheral margin around the open space of the tray;

(b) a thin membrane which covers the open space of the tray and is bonded to the flange peripheral margin, and the membrane forms a sealed reservoir enclosure within the tray interior, and the said membrane is permeable to a volatile medium in the reservoir enclosure;

(c) a volatile air freshener medium which is contained within the reservoir enclosure; and (d) a thin peelable impermeable membrane which is laminated coextensively with the permeable membrane to prevent volatilization of the air freshener medium through the permeable membrane from the reservoir enclosure, wherein the flexible hinge means connecting the cartridge units is structurally adapted to fold the cartridge units exclusively in a tray-bottom to tray-bottom proximity.

2. A dispenser device in accordance with claim 1 wherein the shallow tray is a molded thermoplastic structure.

3. A dispenser device in accordance with claim 1 wherein the shallow tray is a molded polyethylene or polypropylene structure.

4. A dispenser device in accordance with claim 1 wherein the shallow tray has at least one structural reinforcing rib formation extending along the bottom surface of the tray.

5. A dispenser device in accordance with claim 1 wherein the permeable membrane is a polyvinyl thin film.

6. A dispenser device in accordance with claim 1 wherein the impermeable membrane is an aluminum foil or nylon film.

7. A dispenser device in accordance with claim 1 wherein the volatile air freshener is a fragrance in a liquid, gel or crystalline form.

8. A dispenser device in accordance with claim 1 wherein the permeable membrane has transparency, and the content of a volatile air freshener ingredient in the reservoir enclosure is visible.

9. A dispenser device in accordance with claim 1 wherein the outer peelable impermeable membrane is imprinted with a logo design.

10. A dispenser device in accordance with claim 1 wherein the coextensive permeable membrane and peelable impermeable membrane are components of a preformed bonded laminate.

11. A dispenser device in accordance with claim 1 wherein the flexible hinge means connecting the cartridges is a foldable thermoplastic band.

12. A dispenser device in accordance with claim 1 wherein the flexible hinge means connecting the cartridges is a thermoplastic band which has been thermoformed as a unitary structure with the shallow trays of the two cartridges.

13. A dispenser device in accordance with claim 1 wherein the flexible hinge means connecting the cartridge units is structurally adapted to fold the cartridge units exclusively in a tray-bottom to tray-bottom proximity.

* * * * *